United States Patent
Sullivan

(10) Patent No.: US 6,375,621 B1
(45) Date of Patent: *Apr. 23, 2002

(54) PASSIVE APNEA MONITOR

(75) Inventor: Patrick K. Sullivan, Honolulu, HI (US)

(73) Assignee: Ocean Laboratories, Inc., Honolulu, HI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/364,101

(22) Filed: Dec. 27, 1994

Related U.S. Application Data

(63) Continuation of application No. 07/289,689, filed on Dec. 27, 1998, now abandoned, which is a continuation of application No. 07/029,248, filed on Mar. 6, 1987, now abandoned.

(51) Int. Cl.[7] .......................... A61B 5/0205; A61B 5/08
(52) U.S. Cl. ........................ 600/484; 600/529; 600/534
(58) Field of Search ................................ 128/671, 716, 128/721, 722; 600/484, 529, 534, 535

(56) References Cited

U.S. PATENT DOCUMENTS

| | | |
|---|---|---|
| 3,926,177 A | 12/1975 | Hardway, Jr. et al. |
| 3,996,922 A | 12/1976 | Basham |
| 4,033,332 A | 7/1977 | Hardway, Jr. et al. |
| 4,320,766 A | 3/1982 | Alihanka et al. |
| 4,381,788 A | 5/1983 | Douglas |
| 4,403,215 A | 9/1983 | Hofmann et al. |
| 4,438,771 A | 3/1984 | Friesen et al. |
| 4,446,869 A | 5/1984 | Knodle |
| 4,474,185 A | 10/1984 | Diamond |
| 4,494,553 A | 1/1985 | Sciarra et al. |
| RE32,180 E | 6/1986 | Lewiner et al. |
| 4,595,016 A | 6/1986 | Fertig et al. |
| 4,657,026 A | 4/1987 | Tagg |
| 4,757,825 A | 7/1988 | Diamond |
| 4,889,131 A | * 12/1989 | Salem et al. ................. 128/721 |
| 5,002,060 A | * 3/1991 | Nedivi .................... 128/722 X |
| 5,448,996 A | * 9/1995 | Bellin et al. ............ 128/721 X |

FOREIGN PATENT DOCUMENTS

| | | | |
|---|---|---|---|
| DE | 3531399 | 3/1986 | |
| EP | 034077 | 8/1981 | |
| GB | 2138144 | * 10/1984 | ................. 128/721 |
| GB | 2252827 | * 8/1992 | ................. 128/721 |

* cited by examiner

*Primary Examiner*—Lee Cohen
(74) *Attorney, Agent, or Firm*—James Creigton Wray; Meera P. Narasimhan

(57) ABSTRACT

The instrument monitors the acoustic and electromechanical signals of the patient and calculates an energy spectrum periodogram or histogram using time series analysis techniques. The patient lies down on a large piezoelectric film (few microns thick) that has the capability of measuring signals from very high to very low frequencies. The heart and respiration rates as well as obstructive apnea can be observed, detected and measured from the spectral peaks in the resulting energy spectrum. A microcomputing machine provides calculations to determine the energy spectrum and provides for discrimination between noise and a true apnea episode. An alarm calls for assistance in the event of an apnea, including obstructive apnea, or a Sudden Infant Death Syndrome (SIDS) episode.

40 Claims, 1 Drawing Sheet

PASSIVE APNEA MONITOR

This is a continuation of application Ser. No. 07/289,689 filed Dec. 27, 1988, now abandoned, which is a continuation of application Ser. No. 07/029,248 filed Mar. 6, 1987, now abandoned.

BACKGROUND OF THE INVENTION

An interesting application of the proposed technology, to which the invention relates preferably, but not exclusively, is the detection of apnea, the monitoring of biological functions such as heart rate and respiration rates, as well as obstructive apnea, particularly for infants.

SUMMARY OF THE INVENTION

The invention relates to a system that uses acoustic and electromechanical transducers, such as a piezoelectric film, to measure biological respirative signals over time. Time series analysis techniques are then applied to the measured signals whereby an energy spectrum (periodogram/histogram) is calculated that identifies the rhythmic and pseudo-rhythmic biological functions such as respiration and heart rate and obstructions in the breathing passage (obstructive apnea.).

The apnea monitoring instrument offers researchers, clinicians, parents and other people who are involved in child and adult apnea monitoring an inexpensive way to monitor respiration, heart rate and obstructive apnea without the use of restrictive electrical wiring. It makes available a low cost monitoring instrument to be used as a highly reliable tool for researching and monitoring Sudden Infant Death Syndrome (SIDS).

The apnea monitoring instrument could be used in the home for monitoring infants and adults with breathing problems. It could be used for monitoring fetuses in mothers prior to and while giving birth.

It is a particular objective of the invention to improve the sensitivity, reliability, ease-of-use and usefulness of apnea monitors.

The present invention provides a system whereby passive apnea monitoring can occur. This system uses time series analysis of acoustic and electromechanical signals from the patient to calculate an energy spectrum (periodogram/histogram) thereby displaying spectral-peaks that identify heart and respiration rates, and obstructive apnea. A large piezoelectric film with good frequency response characteristics is used to obtain the acoustic and electromechanical signals from the patient. A microcomputer controlled system (comprising of a CPU with associated peripherals) is used to discriminate signal-to-noise considerations and to determine if an apnea episode is occurring. The patient can lie down on the piezoelectric film, similar to an under mattress sheet, so that even when the patient moves around on the mattress a rendering of the patient's heart and respiration rates and air passage into the lungs can be monitored.

The instrument monitors the acoustic and electromechanical signals of the patient and calculates an energy spectrum (periodogram/histogram), using time series analysis techniques. The patient lies down on a large piezoelectric film (few microns thick) that has the capability of measuring signals from very high to very low frequencies. The heart and respiration rates as well as obstructive apnea can be observed, detected and measured from the spectral peaks in the resulting energy spectrum. A microcomputing machine provides calculations to determine the energy spectrum and provides for discrimination between noise and a true apnea episode. An alarm calls for assistance in the event of an apnea, including obstructive apnea, or a Sudden Infant Death Syndrome (SIDS) episode.

A preferred apnea monitoring method communicates a patient's acoustic and electromechanical transmissions to a piezoelectric pad. A voltage signal is produced from the piezoelectric pad, and the voltage signal is transmitted from the piezoelectric pad. The energy spectrum histogram or periodogram is calculated from the transmitted voltage signals, and peaks in the energy spectrum are characterized as heart and respiration rates.

The communicating step comprises communication with pads, in the form of a shirt, sheet or blanket that underlies a patient or a patient's waterbed.

The transmitting step comprises transmitting via electrical wires or fiber optic cables.

The calculating step comprises calculating versus time signals.

The characterizing step comprises measuring and interpreting visually and via a computer or device that characterizes each of the spectral peaks in the energy spectrum.

Preferably the signal is digitized with an analog-to-digital converter using digital techniques, employing a digitized voltage signal versus a digitized time signal, providing the time series and calculating the energy spectrum using techniques including autocovariance techniques, Fast Fourier Transform techniques, and the zero up-crossing techniques.

Significance of spectral peaks is determined, and an alarm is set off in the event of a problem or potential problem related to respiration or heart functions.

Preferably the patient is placed or lies on the piezoelectric film pad which functions to receive the acoustic and electromechanical signals.

In one form, the piezoelectric pad transmits signals using radio communications or other form of communications that does not require electrical wires or fiber optic cables.

Other biological functions of the living body are monitored using the same pad, processor and time series analysis techniques.

A preferred apnea monitor has a piezoelectric pad for producing a voltage signal from a patient's acoustic and electromechanical transmissions. A transmitter is connected to the piezoelectric pad for transmitting the voltage signal from the piezoelectric pad. A processor is connected to the transmitter for receiving the voltage signal and calculating the energy spectrum histogram or periodogram from the voltage signal and time signals. A comparator compares peaks in the energy spectrum and characterizes the peaks as heart and respiration rates.

An analog-to-digital converter is connected to the transmitter and to the processor for providing a digitized signal and facilitating using digital techniques in the processor.

A calculator in the processor uses the digitized voltage signal versus digitized time signals, and provides time series used for calculating the energy spectrum using techniques including, but not limited to, autocovariance techniques, Fast Fourier Transform techniques, and the zero up-crossing techniques.

A display measures and interprets visually peaks in the energy spectrum and via the processor for characterizing each of the spectral peaks.

The piezoelectric pad or pads may take the form of a shirt, sheet or blanket that underlies a patient or a patient's waterbed.

The transmitter comprises electrical wires or fiber optic cables.

An alarm is connected to the processor for determining significance of spectral peaks and setting off the alarm in the event of a problem or potential problem related to respiration or heart functions.

The pad is a piezoelectric film pad and the patient is placed or lies on the piezoelectric film pad which receives the patient's acoustic and electromechanical signals.

One transmitter is a wireless transmitter whereby the piezoelectric pad transmits signals using radio communications or other form of communications that does not require electrical wires or fiber optic cables.

Other biological functions of the living body are monitored using the same system and time series analysis techniques.

These and further and other objects and features of the invention are apparent in the disclosure, which includes the above and ongoing written specification, with the claims and the drawings.

DETAILED DESCRIPTION OF THE PREFERRED EMBODIMENTS

Figure 1:
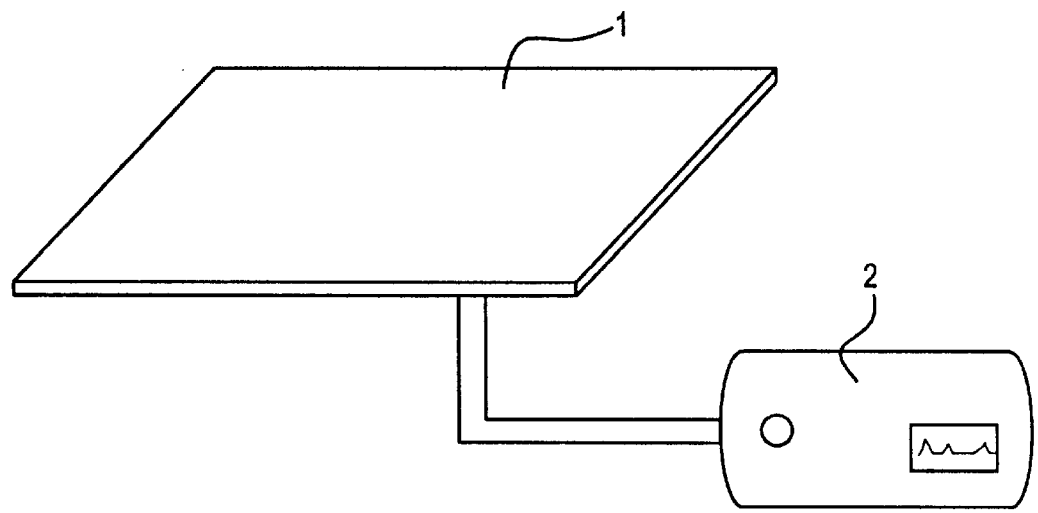
FIG. 1 is a schematic drawing of how the monitoring system works. It shows the piezoelectric film that measures acoustic and electromechanical signals and the basic electronic components required to make a complete instrument.

With reference to FIG. 1, a piezoelectric sheet 1 is connected to a microcomputer 2 (central processing unit—CPU) system that controls time series analysis.

Figure 2:
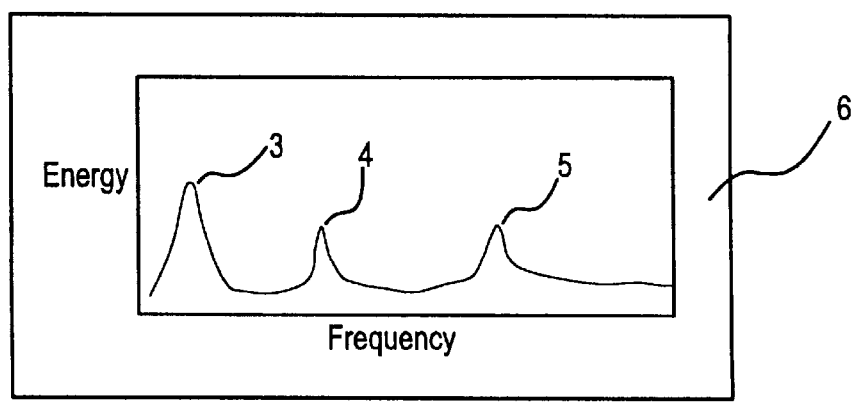
FIG. 2 illustrates the results of time series analysis and identifies cardiac rate, respiration rate and noise generated from the passage of air into the lungs.

FIG. 2 shows results from time series analysis. Spectral peaks for heart rate 3, respiration 4, and air passage 5 are illustrated on the energy versus frequency graph 6.

A passive apnea monitoring instrument uses time series analysis to monitor acoustic signals from the patient. An energy spectrum is thereby created that displays peaks for heart and respiration rates and obstructive apnea. A large piezoelectric film with good frequency response characteristics is used to obtain the acoustic and electromechanical signals from the patient. The patient can lie down on the piezoelectric film, similar to an under mattress sheet, so that even when the patient moves around on the mattress a rendering of the patient's heart and respiration rates and air passage into the lungs can be monitored. A variation of this system includes a large piezoelectric sheet under a mattress filled with water (e.g. waterbed) that allows acoustic coupling between the patient and the piezoelectric pad. That tends to reduce the signal to noise ratio and enhance acoustic coupling.

Various techniques are available for analysis of time series data, e.g. fourier analysis and autocovariance methods. Those methods allow one to obtain pseudo periodic signals from seemingly random data. Peaks are observed for each of the monitored bodily functions. That device could also be used for pregnant women to monitor the bodily functions of the unborn. A mattress sheet or a shirt made of a piezoelectric material with adequate frequency response characteristics will enable the monitoring of acoustic signals from the patient. A microcomputer will interpret the resulting energy spectrum so that the appropriate information will be obtained without requiring a detailed, human-supervised analysis of the resulting spectral information.

Mode of Operation

An example of the mode of operation of the detached apnea monitor instrument is given in the following:

A patient, i.e. an adult or infant, with a heart problem and/or a respiration problem, or a high risk SIDS baby, is monitored by having the patient lie on or sit on a blanket. The blanket contains a piezoelectric material with sufficient frequency response characteristics such that it registers the acoustic and electromechanical signals from the patient. In the event that the heart malfunctions, e.g., high heart rate, low heart rate, etc., and/or the respiration malfunctions, e.g. respiration ceases, or in the event that obstructive apnea occurs, an alarm is sounded so that help can be rendered to the patient. The help that is rendered will be in such a form that normal bodily functions can be resumed, e.g. the administration of CPR. In the event that the patient cannot be revived, them emergency medical personnel must be notified immediately.

While the invention has been described with reference to specific embodiments, modifications and variations of the invention may be constructed without departing from the scope of the invention, which is defined in the following claims.

I claim:

1. An apnea and SIDS monitoring method comprising at least one thin piezoelectric film, communicating a patient's acoustic transmissions to the thin piezoelectric film, producing a voltage signal from the acoustic transmissions in the film pad, transmitting the voltage signal from the film, calculating an energy spectrum from the transmitted voltage signal, and characterizing peaks in the energy spectrum as respiration rates.

2. The method of claim 1, further comprising providing the film in the form of a blanket that underlies a patient on a patient's bed.

3. The method of claim 1, wherein the transmitting step comprises transmitting the voltage signal via electrical wires or fiber optic cables.

4. The method of claim 1, wherein the calculating step comprises calculating the energy spectrum versus time signals.

5. The method of claim 1, wherein the characterizing step comprises measuring and interpreting visually and via a computer or device that characterizes each of the peaks in the energy spectrum.

6. The method of claim 1, further comprising digitizing the signal with an analog-to-digital converter, and employing a digitized voltage signal versus a digitized time signal and providing a time series and calculating the energy spectrum using techniques including autocovariance techniques, Fast Fourier Transform techniques, and the zero up-crossing techniques.

7. The method of claim 1, further comprising determining significance of spectral peaks and setting off an alarm in the event of a problem or potential problem related to respiration.

8. The method of claim 1, wherein the communicating comprises laying the patient on the piezoelectric film, which functions to receive the acoustic transmissions.

9. The method of claim 1, wherein the transmitting comprises transmitting signals from the piezoelectric film using radio communications or other form of communications that do not require electrical wires or fiber optic cables.

10. The method of claim 1, further comprising monitoring other biological functions of the patient using the same film, for communicating and transmitting the functions related signals from the patient and analyzing the transmitted signals.

11. An apnea monitor apparatus comprising a thin piezoelectric film for producing a voltage signal from acoustic sensing transducers in the piezoelectric film of a patient's acoustic transmissions, which are picked up by the film;
   a transmitter connected to the acoustic transducers in the film for transmitting the voltage signal from the film;
   a processor connected to the transmitter for receiving the voltage signal and calculating an energy spectrum from the voltage signal and time signals; and
   a comparator connected to the processor for receiving and comparing peaks in the energy spectrum and characterizing the peaks as respiration rates.

12. The apparatus of claim 11, further comprising an analog-to-digital converter connected to the transmitter and to the processor for providing a digitized signal and facilitating using digital techniques in the processor.

13. The apparatus of claim 11, further comprising a calculator in the processor for using a digitized voltage signal versus digitized time signals, and providing a time series used for calculating the energy spectrum by applying autocovariance techniques, Fast Fourier Transform techniques, and the zero up-crossing techniques.

14. The apparatus of claim 11, further comprising a display for measuring and interpreting visually peaks in the energy spectrum and via the processor for characterizing each of the spectral peaks.

15. The apparatus of claim 11, wherein the film comprises a pad provided in the form of a blanket that underlies a patient or a patient's bed.

16. The apparatus of claim 11, further comprising electrical wires or fiber optic cables connected between the transmitter and the processor.

17. The apparatus of claim 11, further comprising an alarm connected to the processor for determining significance of spectral peaks and for triggering the alarm in the event of a problem or potential problem related to respiration functions.

18. The apparatus of claim 11, further comprising a pad for receiving the film and wherein a patient is placed or lies on the film and pad which receives a patient's acoustic signals.

19. The apparatus of claim 11, wherein the transmitter is a wireless transmitter whereby the transmitter transmits signals from the pad using radio communications or other form of communications that do not require electrical wires or fiber optic cables.

20. The apparatus of claim 11, further comprising means for monitoring other biological functions of the patient with the same film, transmitter, processor and comparator.

21. An apnea and SIDS monitoring method comprising communicating a patient's acoustic and electromechanical transmissions to a piezoelectric pad, producing a voltage signal from the piezoelectric pad, transmitting the voltage signal from the piezoelectric pad, calculating an energy spectrum from the transmitted voltage signal, and characterizing peaks in the energy spectrum as heart and respiration rates.

22. The method of claim 21, further comprising providing the piezoelectric pad in the form of a shirt, or a sheet or blanket that underlies a patient or a patient's waterbed.

23. The method of claim 21, wherein the transmitting step comprises transmitting via electrical wires or fiber optic cables.

24. The method of claim 21, wherein the calculating step comprises calculating the energy spectrum versus time signals.

25. The method of claim 21, wherein the characterizing step comprises measuring and interpreting visually and via a computer or device that characterizes each of the peaks in the energy spectrum.

26. The method of claim 21, further comprising digitizing the signal with an analog-to-digital converter, and employing a digitized voltage signal versus a digitized time signal and providing a time series and calculating the energy spectrum using techniques including autocovariance techniques, Fast Fourier Transform techniques, and the zero up-crossing techniques.

27. The method of claim 21, further comprising determining significance of spectral peaks and setting off an alarm in the event of a problem or potential problem related to respiration or heart functions.

28. The method of claim 21, wherein the communicating comprises laying the patient on the piezoelectric pad which functions to receive the acoustic and electromechanical transmissions.

29. The method of claim 21, wherein the transmitting comprises transmitting signals from the piezoelectric pad using radio communications or other form of communications that do not require electrical wires or fiber optic cables.

30. The method of claim 21, further comprising monitoring other biological functions of the patient using the same pad, for communicating and transmitting the functions related signals from the patient and analyzing the transmitted signals.

31. An apnea monitor apparatus comprising a piezoelectric pad for producing a voltage signal from a patient's acoustic and electromechanical transmissions;
   a transmitter connected to the piezoelectric pad for transmitting the voltage signal from the piezoelectric pad;
   a processor connected to the transmitter for receiving the voltage signal and calculating an energy spectrum from the voltage signal and time signals; and
   a comparator connected to the processor for receiving and comparing peaks in the energy spectrum and characterizing the peaks as heart and respiration rates.

32. The apparatus of claim 31, further comprising an analog-to-digital converter connected to the transmitter and to the processor for providing a digitized signal and facilitating using digital techniques in the processor.

33. The apparatus of claim 31, further comprising a calculator in the processor for using a digitized voltage signal versus digitized time signals, and providing a time series used for calculating the energy spectrum by applying autocovariance techniques, Fast Fourier Transform techniques, and the zero up-crossing techniques.

34. The apparatus of claim 31, further comprising a display for measuring and interpreting visually peaks in the energy spectrum and via the processor for characterizing each of the spectral peaks.

35. The apparatus of claim 31, wherein the pad comprises piezoelectric pads provided in the form of a shirt, or a sheet or blanket that underlies a patient or a patient's waterbed.

36. The apparatus of claim 31, further comprising electrical wires or fiber optic cables connected between the transmitter and the processor.

37. The apparatus of claim 31, further comprising an alarm connected to the processor for determining significance of spectral peaks and for triggering the alarm in the event of a problem or potential problem related to respiration or heart functions.

38. The apparatus of claim 31, wherein the pad is a piezoelectric film pad and a patient is placed or lies on the piezoelectric film pad which receives a patient's acoustic and electromechanical transmissions.

39. The apparatus of claim 31, wherein the transmitter is a wireless transmitter whereby the transmitter transmits signals from the piezoelectric pad using radio communications or other form of communications that do not require electrical wires or fiber optic cables.

40. The apparatus of claim 31, further comprising means for monitoring other biological functions of the patient with the same piezoelectric pad, transmitter, processor and comparator.

* * * * *

UNITED STATES PATENT AND TRADEMARK OFFICE
CERTIFICATE OF CORRECTION

PATENT NO. : 6,375,621 B1
DATED : April 23, 2002
INVENTOR(S) : Patrick K. Sullivan It is certified that error appears in the above-identified patent and that said Letters Patent is hereby corrected as shown below:

Title page,
Item [73], Assignee, "Ocean Laboratories, Inc." should be -- Oceanit Laboratories, Inc. --.

Signed and Sealed this

Twelfth Day of August, 2003

JAMES E. ROGAN
*Director of the United States Patent and Trademark Office*